(12) United States Patent
Shayakhmetov et al.

(10) Patent No.: US 9,982,276 B2
(45) Date of Patent: May 29, 2018

(54) PENTON-MUTATED, INTEGRIN-RETARGETED ADENOVIRUS VECTORS WITH REDUCED TOXICITY AND THEIR USE

(71) Applicant: ADCURE BIOTECHNOLOGIES, LLC., Snellville, GA (US)

(72) Inventors: Dmitry M. Shayakhmetov, Snellville, GA (US); Nelson C. Di Paolo, Avondale Estates, GA (US)

(73) Assignee: ADCURE BIOTECHNOLOGIES, LLC., Snellville, GA (US)

( * ) Notice: Subject to any disclaimer, the term of this patent is extended or adjusted under 35 U.S.C. 154(b) by 76 days.

(21) Appl. No.: 15/067,839

(22) Filed: Mar. 11, 2016

(65) Prior Publication Data

US 2016/0264997 A1 Sep. 15, 2016

Related U.S. Application Data

(60) Provisional application No. 62/131,960, filed on Mar. 12, 2015.

(51) Int. Cl.
*C12N 15/86* (2006.01)

(52) U.S. Cl.
CPC .... *C12N 15/86* (2013.01); *C12N 2710/10022* (2013.01); *C12N 2710/10043* (2013.01); *C12N 2710/10045* (2013.01)

(58) Field of Classification Search
CPC .......... C12N 15/86; C12N 2710/10343; C12N 2810/405; C12N 2810/40; C12N 2810/60; C12N 2810/856; C12N 2710/10043; C12N 2830/008; C07K 14/70546
See application file for complete search history.

(56) References Cited

U.S. PATENT DOCUMENTS

| | | | |
|---|---|---|---|
| 6,951,755 B2 * | 10/2005 | Wickham | C07K 14/005 435/235.1 |
| 9,133,248 B2 * | 9/2015 | Gall | C07K 14/005 |
| 9,682,133 B2 * | 6/2017 | Crystal | A61K 39/0013 |
| 2006/0281090 A1 | 12/2006 | Lieber et al. | |
| 2011/0104788 A1 | 5/2011 | Baker et al. | |
| 2011/0189234 A1 | 8/2011 | Van Beusechem et al. | |

FOREIGN PATENT DOCUMENTS

| | | | | |
|---|---|---|---|---|
| WO | 199214755 A1 | 9/1992 | | |
| WO | 02081497 A2 | 10/2002 | | |
| WO | WO2011057248 | * | 5/2011 | ........... C07K 14/005 |
| WO | WO2011116189 | * | 9/2011 | ........... C07K 14/005 |

OTHER PUBLICATIONS

Schoggins et al. (J. Virology, 2006, vol. 80, No. 21, pp. 10634-10644).*
International Search Report and Written Opinion, issued in PCT/US2016/013765, dated Jun. 30, 2016.
Kalyuzhniy, O., et al. "Adenovirus serotype 5 hexon is critical for virus infection of hepatocytes in vivo," Proceeding of the National Academy of Science of the U.S.A., Apr. 7, 2008, vol. 105, No. 14, pp. 5483-5488.

* cited by examiner

*Primary Examiner* — Bao Q Li
(74) *Attorney, Agent, or Firm* — Andrews Kurth Kenyon LLP; Michael Ye

(57) ABSTRACT

The present invention describes generation and the use of adenovirus variants (Ad) possessing modified capsid penton base protein where mutations in the penton based RGD loop are made to avoid Ad binding to cellular β3-integrins. Specifically, the ablation of Ad penton base interaction with cellular β3-integrins results in reduced activation of inflammation after intravenous Ad administration. Further, the introduction into penton RGD loop of non-RGD containing peptides, which mediate virus entry into the cell via new cellular receptors, allows for the efficient Ad-mediated gene delivery into target cells in vivo after intravascular virus administration and triggers significantly reduced toxicity associated with Ad injection.

10 Claims, 8 Drawing Sheets

Functional effect:
No binding to cell β3 integrins

Wild type Ad5 penton base RGD-containing loop

DAYQAS - LLKDDT EQGGGGAGGS NSSGSGAEENSNAAAAAMQPVEDM
NDHAIRGDTFATRAEEKRAEAEAAAEAAAPAAQPEV EKP - QKKPVIK PLTEDSK

 RGD-loop-deleted penton base

DAYQAS - LLKDDT EQGG GG EKP - QKKPVIK PLTEDSK

FIG. 3B.

Wild type Ad5 penton base RGD-containing loop

DAYQAS - LLKDDT EQGGGGAGGS NSSGSGAEENSNAAAAAMQPVEDM
NDHAIRGDTFATRAEEKRAEAEAAAEAAAPAAQPEV EKP - QKKPVIK PLTEDSK

 RGD-Loop-mutated penton base

DAYQAS - LLKDDT EQGGGG EQGGGGAGGS NSSGSGAEEN
SNAAAAAMGSG <u>CNGQGEQC</u> AAAEAAAPAAQPEV EKP - QKKPVIK
PLTEDSK

 α3β1-integrin-binding peptide

DAYQAS - LLKDDT EQGGGG EQGGGGAGGS NSSGSGAEEN
SNAAAAAMGSG <u>RKKRRQRRR</u> AAAEAAAPAAQPEV EKP - QKKPVIK
PLTEDSK

 αvβ5-integrin-binding peptide

```
                323                                              356
Ad5-GFP   N A A A A A M Q P V E D M N D H A I R G D T F A T R A E - - - - - - -
dRGD      N A A A A A M Q P V E D M N D H A I - - - T F A T R A E - - - - - - -
Lam1      N A A A S G T F L L I S Q A R K Q A A S I K V A V S A D R K G - - -
Lam3      N A A A S G T R E L I Q A R D A A S K V A V P K R N G K S G V E V
                357                                              391
Ad5-GFP   - - - - - E K R A E A E A A A E A A A P A A Q P E V E K P Q K K P V
dRGD      - - - - - E K R A E A E A A A E A A A P A A Q P E V E K P Q K K P V
Lam1      - - - - I K A Y N P Q I S S T N Y N P L T G S T G G A K P Q K K P V
Lam3      R L F N D L E D L F G Y T S L S E G S T G G A P E V E K P Q K K P V
```

Penton RGD loop substitution in Ad-Lam 1 and Ad-Lam3

PENTON-MUTATED, INTEGRIN-RETARGETED ADENOVIRUS VECTORS WITH REDUCED TOXICITY AND THEIR USE

CROSS-REFERENCE TO RELATED APPLICATION

This United States Patent Application claims the benefit under 35 U.S.C § 119(e) of U.S. Provisional Patent Application No. 62/131,960, filed Mar. 12, 2015, the content of which is hereby incorporated by reference. This invention was made with funds from the U.S. National Institutes of Health Grant No. AI065429. Accordingly, the United States Government has certain rights in this invention.

STATEMENT REGARDING SEQUENCE LISTING

The sequence listing associated with this application is provided in text format in lieu of a paper copy and is hereby incorporated by reference into the specification. The name of the text file containing the sequence listing is PentonSeq20160310.txt. The text file is 2 KB, was created on Mar. 10, 2016; and is being submitted via EFS-Web with the filing of the specification.

FIELD OF THE INVENTION

This invention relates to the field of gene therapy, and in particular, to novel adenovirus (Ad) vectors and virus variants with mutations in penton base protein, which efficiently deliver genes of interest to hepatocytes or other target cells after intravascular administration and demonstrate significantly reduced activation of inflammation, and thus can be targeted to selectively infect cells and tissues for gene therapy.

BACKGROUND OF THE INVENTION

The application of Adenoviruses (Ad) as vectors for therapeutic gene delivery, vaccines, or cancer therapy is a very promising approach for treatment of a variety of highly prevalent and clinically important diseases. Ad vectors form highly stable proteinaceous particles that can efficiently deliver therapeutic transgenes into both dividing and quiescent cells. Other advantages of Ad vectors as gene therapy tools include: capacity for delivery of large therapeutic genes, the ease of genetic manipulation, the ability to produce large quantities of clinical grade vectors, and the episomal nature of the vector genome. However, the successful application of Ad vectors for gene therapy applications in clinical settings has been hampered by the unexpected complexity of the vector-host interactions. Interactions between the Ad particles and the cell and factors of the immune system in humans may result in severe virus-induced toxicity and therefore dire clinical outcomes. One of the harshest setbacks in Ad vector therapeutic development was caused by the death of a patient enrolled in a clinical trial in 1999 (Raper et al., 2003). After infusion of Ad vector into hepatic artery, the patient died due to the severe Ad vector-induced inflammatory response, which resulted in multiple organ failure, disseminated intravascular coagulation, and a cytokine storm (Raper et al., 2003; Raper et al., 2002). Clearly, detailed and thorough understanding of the host response to intravascular Ad vector administration is a crucial prerequisite for the successful and safe use of Ad vectors in humans.

Our previous studies indicate that the activation of pro-inflammatory cytokines and chemokines by tissue residential macrophages in vivo occurs downstream of the IL-1α-IL-1RI signaling pathway and is triggered by adenovirus Arginine-Glycine-Aspartic acid, RGD, motif-dependent binding to macrophage β3 integrins (Di Paolo et al., 2009). The RGD motif, located within a flexible and highly variable loop of the adenovirus penton base protein, which is considered the functional moiety of the capsid that facilitates virus internalization into cells by promoting integrin clustering at the sites of virus attachment and viral endocytosis. Accordingly, RGD motif-deleted viruses demonstrate reduced efficacy of internalization into cells, a feature that is not conducive to efficient vector-mediated gene transfer.

In vitro studies demonstrated that Ad infection starts with the virus binding to a high affinity primary attachment receptor on the cell surface (Nemerow, 2000). The trimeric Ad fiber protein mediates this interaction when its distal knob domain binds to a specific cellular receptor. For binding to cells, species A, C, D, E, and F human Ad may utilize the coxsackievirus and Ad receptor (CAR) (Roelvink et al., 1998); however, the majority of human species B Ads utilize CD46 as a high affinity cellular attachment receptor (Gaggar et al., 2003). In this regard, soluble Ad fiber or anti-fiber antibodies can inhibit infection by the Ad.

Fiber-mediated binding of Ad to cells is followed by RGD motif-mediated binding of the viral penton base protein to cellular integrins (e.g., αvβ3 and αvβ5) (Nemerow and Stewart, 1999). This interaction induces integrin activation and cytoskeleton rearrangement that facilitates internalization of the virus particle into the cell. Therefore, Ad penton interaction with cellular integrins is necessary for efficient virus entry into the cell, cell transduction and gene transfer to occur. Based in part on this knowledge, previous disclosure provided Ad vectors that were designed to change Ad interactions with integrins in the in vitro cell culture systems. See U.S. Pat. No. 5,712,136, which is incorporated by reference herein. However, in the in vitro systems, such as 293 cell line, which is widely used for growing of newly constructed Ad vectors and for preparation of high-titer vector stocks suitable for pre-clinical and clinical applications, Ad interactions with integrins play insignificant role in supporting virus cell infection. Indeed, Ad mutants, which are deleted for and lack RGD amino acid motif in penton protein (AdΔRGD, refs) can be grown to high titers and are efficiently propagated on 293 cells in vitro (Shayakhmetov et al., 2005). Importantly, the U.S. Pat. No. 5,712,136 does not teach of constructing Ads for in vivo applications, and capable of triggering reduced inflammatory responses and transducing cells in the body after intravascular administration.

For successful application of Ad vectors for correcting human genetic diseases and for the treatment of disseminated and localized metastatic cancers, Ad vectors with improved safety profiles are critically needed. Furthermore, what is needed are new Ad vectors that exhibit efficient cell transduction and reduced activation of inflammation after intravascular injection.

SUMMARY

The present invention provides for novel capsid-modified Ads carrying reporter transgene, therapeutic transgene, and/or genetic mutations to enable tumor-selective virus replication, and possess mutation(s) within penton base protein (a.k.a. adenovirus structural protein III) in order to structurally and functionally abrogate virus interaction with cellular β3-integrins that are expressed on host cells in the body, specifically but without limitations on macrophages, endothelial, hematopoietic cells, and platelets, and, upon virus binding to which, activate inflammatory response and contribute to virus sequestration from the blood away from the cells of interest.

Embodiments can include one or more of the following features.

The recombinant adenovirus of the invention (FIGS. 1A, 1B, 7B) provides a novel design of a set of mutations that allow for escaping virus interaction with host β3 integrins and, therefore, exhibits greatly reduced activation of inflammation after intravascular virus delivery. In particular, the present invention provides a recombinant, double-stranded, adenovirus where the single virus genomic DNA molecule possesses genetic mutation(s) in penton base protein to ablate Ad interactions with cellular integrins, in particular of β3 class.

Specific mutations ablating penton base protein interaction with cellular β3-integrins include, for example for human Ad serotype 5 virus, mutation, deletion, or substitution of amino acids RGD within Ad5 penton RGD loop (FIG. 3A, 3B, 4A).

In a preferred embodiment of this invention, the specific mutations ablating penton interactions with cellular β3-integrins include mutations, deletion, or substitution of an RGD motif containing penton base loop with iso-functional amino acid sequences (for example, but without limitation, integrin-interacting amino acid sequences naturally occurring in human laminins 1 or 3 and lacking RGD motif) that enable virus interaction with non-natural cellular Ad receptors that functionally allow for and enable virus attachment to the cell and cell entry (FIG. 4A).

The adenovirus vector of this invention with mutated penton RGD loop as described above can possess additional mutations within its fiber or hexon proteins to improve in vivo virus pharmacokinetic and pharmacodynamics and further enable cell-type-specific virus targeting after intravascular administration. The adenovirus of the invention can also possess genetic mutations in virus-encoded non-structural proteins to enable its tumor cell-specific replication. The adenovirus vector described in this invention can be based on human species C adenovirus serotype 5, Ad5, or any other human or animal adenovirus serotype.

The adenovirus of the invention can be administered intravenously with or without pharmacological conditioning of the host to reduce virus trapping in Kupffer cells, which can accumulate adenovirus via mechanisms unrelated to cellular integrins.

DESCRIPTION OF THE DRAWINGS

FIG. 2 is amino acid sequence alignment of RGD loop of the penton base proteins (pIII) for human adenovirus serotypes from different subgroups (species).

FIG. 3A is an example of deletion of an RGD-motif-containing loop, which ablates penton binding to cellular integrins.

FIG. 3B is an example of a substitution of an RGD motif for non-RGD motif-containing peptides, capable of selectively driving penton interactions with specific integrins (SEQ. No. 3 and SEQ. No. 4), present on tumor cells, but not abundantly expressed on the liver cells.

DETAILED DESCRIPTION OF THE INVENTION

Figure 1A:
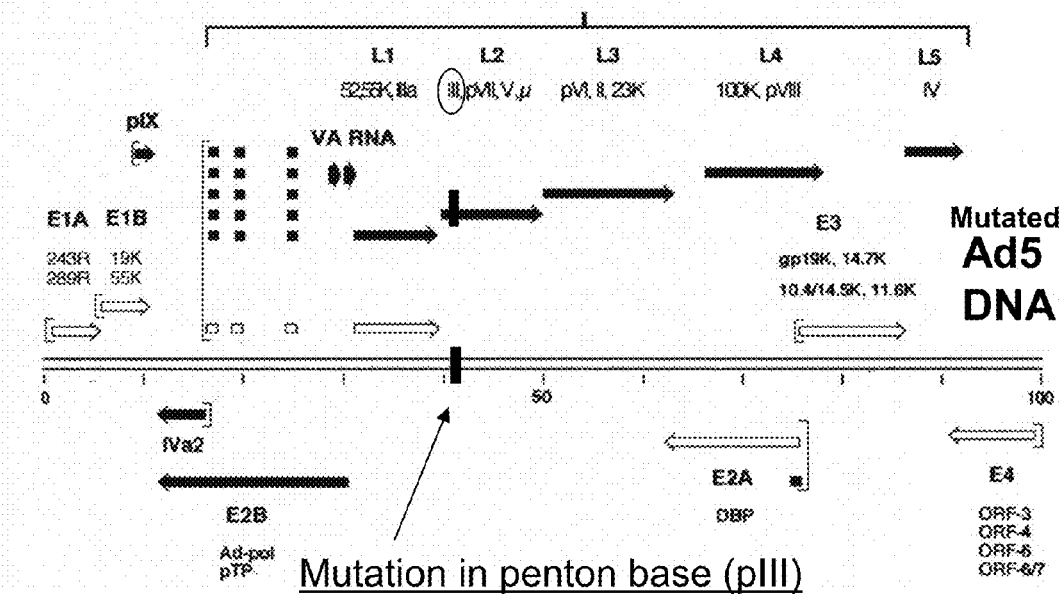
FIG. 1A is a schematic of a single adenovirus genomic DNA possessing mutations in penton base (pIII) protein, preventing virus interactions with cellular integrins that bind RGD amino acid motif, including β3-integrins.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

Unless defined otherwise, all technical and scientific terms used herein have the same meaning as commonly understood by one of ordinary skill in the art to which this invention belongs. For purposes of the present invention, the following terms are defined below.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

In one aspect, the present invention provides for novel modified Ad vectors. Adenovirus (also referred to herein as "Ad") is a ubiquitous pathogen causing a wide range of human diseases, which include respiratory tract infections, conjunctivitis, hemonhagic cystitis, and gastrointestinal diseases (Shenk, 1996, 2001). In immunocompetent patients, Ad infection is self-limited, and after resolution of the acute infection, the virus remains latent in lymphoid and renal tissues. In contrast, in immunocompromised patients Ad may cause life threatening or even fatal fulminant hepatitis and disseminated infection of other tissues (Kojaoghlanian et al., 2003).

There are currently 60 characterized human Ad serotypes which are divided into seven species (formally subgroups) from A to G (Alonso-Padilla et al., 2015). Eighty percent pediatric patients develop antibodies to at least one of many Ad serotypes by the age of 5 (Barouch et al., 2011; Bradley et al., 2012; Roberts et al., 2006) The prevalence of human Ad species C-specific antibodies in these populations reaches as high as 50 to 80% (Alonso-Padilla et al., 2015; Barouch et al., 2011). Although various Ad serotypes may initiate infection via different transmission routes, and by utilizing distinct virus attachment receptors, the host factors and cell types controlling tissue specificity of Ad infection in vivo remain insufficiently understood.

The Ad genome is a double-stranded linear DNA molecule of about 36 kilobases containing genes encoding the viral proteins. At the ends of the Ad genome, inverted repeats (also referred to as inverted terminal repeats or ITRs) contain replication and the encapsidation regions. The early genes are distributed in four regions dispersed in the Ad genome (designated E1 to E4). The early genes are expressed in six transcriptional units. The late genes (designated Li to L5) partly overlap with the early transcription units and are generally transcribed from the major late promoter (referred to as MLP) (Shenk, 2001).

The Ad infectious cycle occurs in two steps. The early phase precedes the initiation of replication and makes it possible to produce the early proteins regulating the replication and transcription of the viral DNA. The replication of the genome is followed by the late phase during which the structural proteins that constitute the viral particles are synthesized. The assembly of the new virions takes place in the host cell nucleus. In a first stage, the viral proteins assemble so as to form empty capsids of icosahedral structure into which the genome is encapsidated. The assembled virus includes a penton base and fiber. The Ads liberated are capable of infecting other permissive cells. The fiber and the penton base present at the surface of the capsids play a role in the cellular attachment of the virions and their internalization.

In vitro studies demonstrated that Ad infection starts with the virus binding to a high affinity primary attachment receptor on the cell surface (Nemerow, 2000). The trimeric Ad fiber protein mediates this interaction when its distal knob domain binds to a specific cellular receptor. For binding to cells, species A, C, D, E, and F human Ad may utilize the coxsackievirus and Ad receptor (CAR) (Roelvink et al., 1998); however, the majority of human species B Ad utilize CD46 as a high affinity cellular attachment receptor (Gaggar et al., 2003). In this regard, soluble Ad fiber or anti-fiber antibodies can inhibit infection by the Ad. Fiber-mediated binding of Ad to cells is followed by RGD motif-mediated binding of the viral penton base protein to cellular integrins (e.g., $\alpha_v\beta_3$ and $\alpha_v\beta_5$) (Nemerow and Stewart, 1999). This interaction induces integrin activation and cytoskeleton rearrangement that facilitates internalization of the virus particle into the cell.

Based in part on this knowledge, previous disclosure provided Ad vectors that were designed to change Ad interactions with integrins in the in vitro cell culture systems. See, e.g., U.S. Pat. No. 5,712,136, which is incorporated by reference herein. However, the patent above does not teach of constructing Ads for in vivo applications, capable of triggering reduced inflammatory responses after intravascular injection. Importantly, in vitro propagation and virus growth in 293 cells for the purpose of pre-clinical- and clinical-grade vector production is not affected to a large degree by the complete lack of RGD motif in the penton protein and occurs with high efficiency for vectors deleted for RGD amino acid motifs in the penton protein, AdΔRGD (Shayakhmetov et al., 2005).

Ads are used in an increasing number of applications for gene transfer. Ads have been identified in numerous animal species. They exhibit low pathogenicity in immune-competent individuals, and replicate both in dividing and quiescent cells. Ads generally exhibit a broad host spectrum and are capable of infecting a very large number of cell types, such as epithelial cells, endothelial cells, myocytes, hepatocytes, nerve cells, and synoviocytes, among many other cell types.

Recombinant Ad vectors are derived from Ads and usually include cis acting regions that are necessary for the replication of the virus in the infected cell (e.g., the ITRs and encapsidation sequences). Recombinant Ad vectors can also contain substantial internal deletions designed to remove or modify viral genes, to allow for the insertion of a heterologous gene(s) for gene transfer. To accommodate heterologous genes, Ads used in gene transfer protocols can be made deficient for replication by deletion of at least the E1 region and are propagated in a complementation host cell line that provides the deleted viral function(s) in trans. One commonly used host cell line, the 293 line, was established from human embryonic kidney cells and provides the Ad E1 function in trans.

Gene delivery systems based on human species C Ad serotype 5 (Ad5) are among the most frequently used in clinical studies, which aim to correct human genetic and acquired diseases, including cancer. The extreme propensity of the virus for hepatocyte infection following its intravascular delivery has made Ad5 the vector of choice for applications requiring high level transgene expression in hepatocytes in vivo. However, the efficient interaction between Ad5 and liver cells, which sequester over 90% of the delivered vector dose (Alemany and Curiel, 2001; Alemany et al., 2000; Worgall et al., 1997), represents a significant hindrance if gene delivery to extra-hepatic cells and tissues, such as disseminated metastatic cancer cells and tissues, is required. From in vitro analyses it was found that Ad5 infection is initiated when the minor capsid protein, fiber, binds to CAR on the cell surface (Bergelson et al., 1997). Subsequent binding of the penton base protein to cellular integrins facilitates internalization of the attached particle into the cell (Wickham et al., 1993). Although both CAR and integrin binding are important for cell infection in vitro, neither of these interactions are essential for Ad5 entry into hepatocytes in vivo (Alemany and Curiel, 2001; Shayakhmetov et al., 2004).

Ad sequestration in liver resident macrophages, Kuppffer cells (Lieber et al., 1997), and macrophages residing in other organs of the body, such as spleen (Di Paolo et al., 2009), leads to activation of inflammatory cytokines and chemokines, induction of pro-inflammatory-type of cell death (Manickan et al., 2006), rapid release on polymorphonuclear leukocytes from the bone marrow into the blood (Di Paolo N C, 2014) and systemic toxicity manifested by elevated levels of pro-inflammatory mediators in the blood, systemic complement activation, followed by leukocytopenia. Acute systemic inflammatory response associated with intravenous administration of Ad represents the key barrier for escalating Ad doses to a level that is therapeutic in gene transfer applications or transduction of metastatic tumors.

Figure 1B:
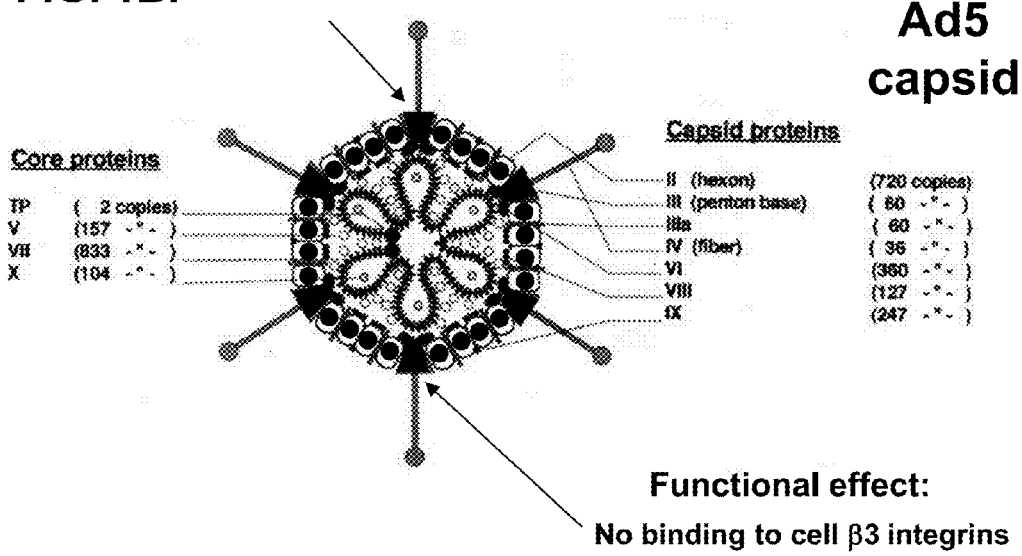
FIG. 1B is a schematic of a single adenovirus particle capsid possessing mutations in penton base (pIII) protein, preventing virus interactions with cellular integrins that bind RGD amino acid motif, including β3-integrins.
Figure 7A:
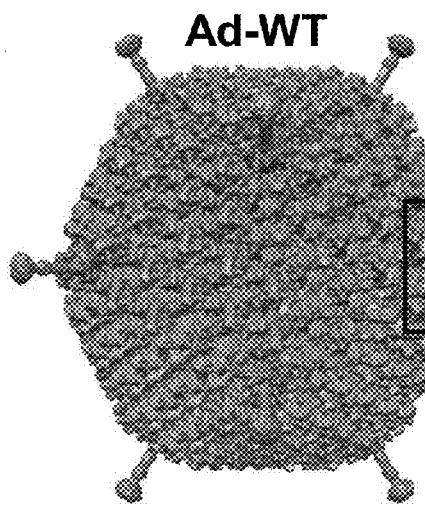
FIG. 7A is a picture showing human adenovirus single particle image reconstruction based on cryo-electron microscopy analysis. Ad-WT is adenovirus vector comprising naturally-occurring penton and hexon proteins.
Figure 7B:
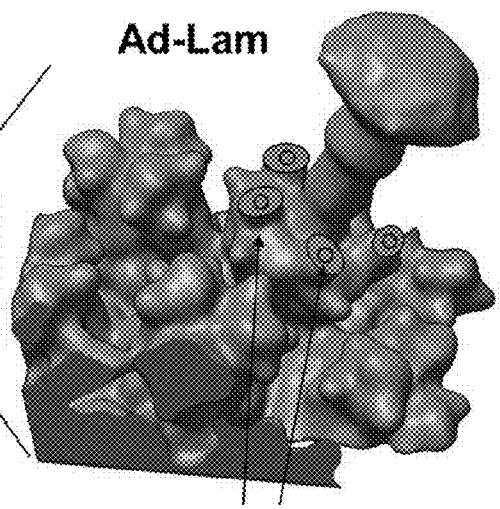
FIG. 7B is a structural depiction of mutations in exposed penton RGD amino acid loop shown on cryo-electron microscopy reconstruction of individual virus particle of Ad. The locations of RGD loop substitutions in penton protein are shown by arrows.

The present invention provides for the recombinant adenovirus (FIGS. 1A, 1B, 7A) with a novel set of mutations that allow for escaping virus interaction with host β3 integrins and, therefore, allowing the virus to exhibits greatly reduced activation of inflammation after intravascular injection. In particular, the present invention provides a recombinant, double-stranded, adenovirus where the single virus genomic DNA molecule (FIG. 1A) comprises genetic mutation(s) in penton base protein introduced to ablate Ad interactions with cellular integrins, in particular of β3 class.

In certain embodiments, specific mutations ablating penton base protein interaction with cellular β3-integrins include, for example for human Ad serotype 5 virus, mutation, deletion, or substitution of amino acids Arginine-Glycine-Aspartic acid, RGD motif, within Ad5 penton flexible and surface-exposed loop known as RGD loop (FIG. 3A).

Figures 4A, 4B:
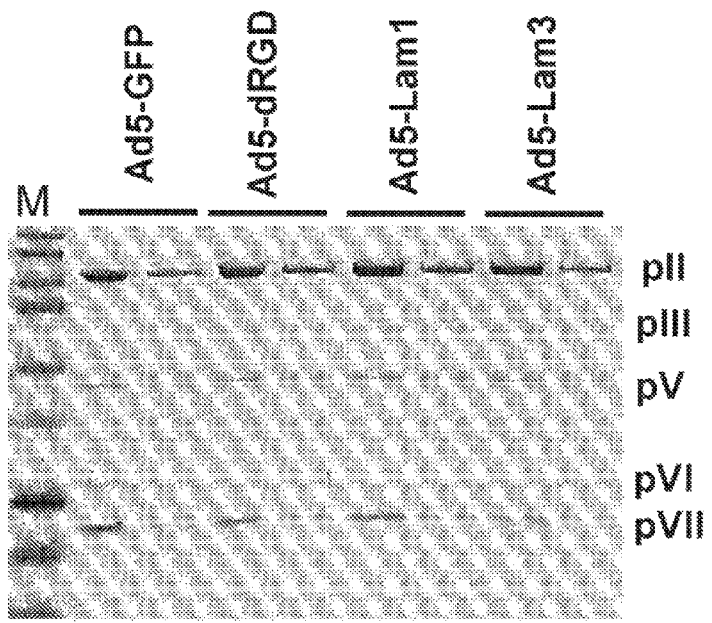
FIG. 4A shows specific examples of mutations introduced into Ad5 penton RGD loop where the entire RGD loop is deleted (dRGD) and the exact amino acid sequence of large non-RGD peptides from human laminins 1 and 3 that were introduced into Ad5 penton instead of RGD loop (Lam1, SEQ. No. 1; and Lam3, SEQ. No. 2, respectively). Naturally occurring amino acid sequence in human Ad serotype 5 is also shown (Ad5-GFP).
FIG. 4B is protein gel analysis of virus particle composition for all indicated vectors shown after Coomassie staining of poly-acrylamide gel. Two 2-fold distinct concentrations of virus particles loaded on the gel are shown for each vector.

In a preferred embodiment of this invention, the specific mutations ablating penton interactions with cellular β3-integrins include mutations, deletion, or substitution of an RGD motif containing penton base loop with iso-functional amino acid sequences. These iso-functional amino acid sequences may, for example, but not exclusively, include amino acid sequences naturally occurring in human laminins 1 (SEQ. No. 1) or laminin-3 (SEQ. No. 2), which enable virus interaction with non-natural cellular Ad receptors that functionally allow for and enable virus attachment to the cell and cell entry (FIG. 4A).

The Ad vector penton sequence can be a hybrid and can comprise fragments of diverse origins, and can comprise naturally-occurring or non-naturally-occurring sequences. In certain embodiments, the penton gene is derived from a human Ad, such as those of serotype C and, in particular, the type 2 or 5 Ads (Ad2 or Ad5).

In another embodiment, the adenovirus vector of this invention with mutated penton RGD loop as described above can possess additional mutations within its fiber or hexon proteins to improve in vivo virus pharmacokinetic and pharmacodynamics and further enable cell-type-specific virus targeting after intravascular administration.

In another embodiment, the adenovirus of the invention can also possess genetic mutations in virus-encoded non-structural proteins to enable its tumor cell-specific replication. The adenovirus vector described in this invention can be based on human species C adenovirus serotype 5, Ad5, or any other human or animal adenovirus serotype.

In yet another embodiment, the adenovirus of the invention can express transgene or transgenes that can have a "reporter", diagnostic, or therapeutic purposes.

As yet another embodiment of the invention, a single virus can further be engineered to have properties described above and combinations thereof.

The adenovirus of the invention can be administered intravenously with or without pharmacological conditioning of the host to reduce virus trapping in Kupffer cells, which can accumulate adenovirus via mechanisms unrelated to cellular integrins.

As noted above, the Ad vectors described herein can be based on human Ad serotype 5 (Ad5); however the Ad vectors can be based on any other human or animal Ad serotype. For example, non-human Ads can include canine, avian, bovine, murine, ovine, porcine or simian origin.

In certain embodiments, the Ad can be a recombinant and replication-defective Ad (i.e., incapable of autonomously replicating in a host cell). Such a replication-deficient Ad can include, for example, a mutation or deletion of one or more viral regions, such as, for example, all or part of the E1 region and/or E3 region. The genome of an Ad optionally can include additional deletions or mutations affecting other regions, such as, for example, the E2, E4 and/or L1-L5 regions, including complete deletion of the virus coding sequences and replacement with non-Ad DNA (so called "helper-dependent" vectors).

The Ad vectors can optionally be recombinant Ads and comprise one or more genes of interest contained within a nucleic acid segment, which is introduced into the Ad vectors. The genes of interest can be placed under the control of the elements necessary for their expression in a host cell. The gene of interest is typically a human or non-human heterologous gene (i.e., a non-Ad gene). The gene of interest can be, for example, genomic, cDNA (complementary DNA), a hybrid or chimeric gene (e.g., a minigene lacking one or more introns), or the like. It can be obtained, for example, by conventional molecular biology techniques and/or by chemical synthesis. A gene of interest can encode, for example, an antisense RNA, shRNA, lncRNA, or siRNA, a ribozyme or an mRNA that can be translated into a polypeptide of interest. A polypeptide of interest can be, for example, a nuclear, cytoplasmic, membrane, secreted or other type of protein. Further, the polypeptide of interest can be, for example, a polypeptide as found in nature, a chimeric polypeptide obtained from the fusion of sequences of diverse origins, or of a polypeptide mutated relative to the native sequence having improved and/or modified biological properties.

In certain embodiments, the nucleic acid segment can comprise a predetermined gene of interest that is configured to achieve a predetermined function or outcome. The gene of interest can encode, for example and without limitation, one of the following polypeptides: cytokines or lymphokines (α-, β- or γ-interferon, interleukins (e.g., IL-1α, IL-2, IL-6, IL-10, IL-12, IL-15, IL-15R, and IL-24), tumor necrosis factors (TNF), colony stimulating factors (e.g., GM-CSF, C-CSF, M-CSF, or the like)); cellular or nuclear receptors (e.g., those recognized by pathogenic organisms (e.g., viruses, bacteria or parasites)); proteins involved in activation of innate immune signaling of prokaryotic or eukaryotic origin (e.g. bacterial flagellin, or the like); proteins involved in triggering a genetic diseases (e.g., factor VII, factor VIII, factor IX, dystrophin or minidystrophin, insulin, CFTR protein (Cystic Fibrosis Transmembrane Conductance Regulator)); growth hormones (e.g., insulin, hGH or the like); enzymes (e.g., urease, renin, thrombin, or the like); enzyme inhibitors (e.g., α1-antitrypsin, antithrombin III, viral protease inhibitors, or the like); polypeptides with antitumor effect (e.g., which are capable of at least partially inhibiting the initiation or the progression of tumors or cancers), such as antibodies, inhibitors acting on cell division or transduction signals, products of expression of tumor suppressor genes (specifically, but without limitation, p53 or pRb), proteins stimulating the immune system, or the like); proteins of the class I or II major histocompatibility complex or regulatory proteins acting on the expression of the corresponding genes; polypeptides capable of inhibiting a viral, bacterial or parasitic infection or its development (e.g., antigenic polypeptides having immunogenic properties, antigenic epitopes, antibodies, transdominant variants capable of inhibiting the action of a native protein by competition, or the like); toxins (e.g., herpes simplex virus 1 thymidine kinase (HSV-1-TK), ricin, cholera toxin, diphtheria toxin, or the like) or immunotoxins; markers (13-galactosidase, luciferase, Green Fluorescent Protein, or the like); polypeptides having an effect on apoptosis (e.g., inducer of apoptosis: Bax, or the like, blocker of apoptosis Bcl2, Bclx, or the like); cytostatic agents (e.g., p21, p16, Rb, or the like); apolipoproteins (e.g., apoE or the like); superoxide dismutase, catalase, nitric oxide synthase (NOS); growth factors (e.g., Fibroblast Growth Factor (FGF), Vascular Endothelial Cell Growth Factors (VEGFs), insulin, or the like), or others genes having therapeutic or research interest. It should be noted that this list is not limiting and that other genes can also be used. In certain embodiments, the polypeptide of interest is not a marker (e.g., β-galactosidase, luciferase, Green Fluorescent Protein, GFP, or the like).

The Ad optionally can include a selectable gene which allows for selection or identification of the infected cells. Suitable selectable genes include, for example, Neo (encoding neomycin phosphotransferase), DHFR (Dihydrofolate Reductase), CAT (Chlorainphenicol Acetyl transferase), PAC (Puromycin Acetyl-Transferase), GPT (Xanthine Guanine Phosphoriboxyl Transferase), or the like. In other embodiments, the Ad is free of selectable genes.

In certain embodiments, the gene of interest can optionally include elements necessary for the expression of the gene in a host cell. Such elements include, for example, elements facilitating transcription of the gene into RNA and/or the translation of an mRNA into a protein. Suitable promoters include, for example, those of eukaryotic or viral origin. Suitable promoters can be constitutive or regulatable (e.g., inducible). A promoter can be modified to increase promoter activity, suppress a transcription-inhibiting region, make a constitutive promoter regulatable, or the like, introduce a restriction site, or the like. Examples of suitable promoters include, for example, the CMV (Cytomegalovirus) viral promoter, the RSV (Rous Sarcoma Virus) viral promoter, the promoter of the HSV-1 virus TK gene, the early promoter of the SV4O virus (Simian Virus 40), the Ad MLP promoter, the eukaryotic promoters of the murine or human genes for PGK (Phospho Glycerate kinase), MT (metallothionein), α1-antitrypsin and albumin (liver-specific), immunoglobulins (lymphocyte-specific), a tumor-specific promoter (e.g., α-fetoprotein, AFP); MLJC-1; prostate specific antigen (PSA); and flt1 specific for endothelial cells.

A gene of interest can also include additional elements for the expression (e.g., an intron sequence, a signal sequence, a nuclear localization sequence, a transcription termination sequence, a site for initiation of translation of the IRES type, or the like), for its maintenance in the host cell, or the like.

Further provided herein is a host cell infected with an Ad according to the present disclosure or capable of being obtained by a method according to the present invention. The infected host cell can be, for example, a mammalian cell, such as a human cell, or a non-human, animal cell. An infected host cell also can be, for example, a primary or tumor cell and of any suitable origin, for example, of hematopoietic (e.g., a totipotent stem cell, leukocyte, lymphocyte, monocyte or macrophage, or the like), muscle (e.g., a satellite cell, myocyte, myoblast, smooth muscle cell), cardiac, nasal, pulmonary, tracheal, hepatic, epithelial or fibroblast origin.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Viral Promoters and Enhancers

Preferred promoters controlling transcription from vectors in mammalian host cells may be obtained from various sources, for example, the genomes of viruses such as: polyoma, Simian Virus 40 (SV40), Ad, retroviruses, hepatitis B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355 360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin (bp 100 270), the cytomegalovirus early promoter enhancer, the polyoma enhancer on the late side of the replication origin, and Ad enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410 413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

It is understood that any of the methods typically can be used and that in certain instances the results of these various methods may differ, but the skilled artisan understands if identity is found with at least one of these methods, the sequences would be said to have the stated identity, and be disclosed herein.

Pharmaceutical Carriers/Delivery of Pharmaceutical Products

In one aspect, it is understood and herein contemplated that the novel Ads of the present invention and nucleic acids can be used as a component in a pharmaceutical composition for therapeutic or prophylactic purposes. In one aspect, provided herein are pharmaceutical compositions comprising any of the Ads, Ad vectors, and nucleic acids disclosed herein. It is understood and herein contemplated that for reasons well-known in the art, it may be advantageous for any pharmaceutical composition to comprise a replication-defective or replication-attenuated recombinant Ad. In one aspect, the pharmaceutical composition can comprise an Ad, wherein the Ad is a replication-competent or replication-restricted to replicate in tumor cells only recombinant Ads.

Further provided are pharmaceutical compositions comprising a therapeutic or prophylactic agent, a host cell or an Ad, in combination with a pharmaceutically acceptable carrier. In certain embodiments, the composition can be used for preventive and/or treatment of diseases, such as genetic diseases (e.g., hemophilia, cystic fibrosis, diabetes, Duchenne's myopathy or Becker's myopathy, or the like), localized and disseminated metastatic cancers of solid or hematologic origin, including those induced by oncogenes or viruses, viral diseases, such as hepatitis B or C and AIDS (acquired immunodeficiency syndrome resulting from HIV infection), recurring viral diseases, such as viral infections caused by the herpesvirus and cardiovascular diseases including restenosis.

Accordingly, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells).

Pharmaceutically Acceptable Carriers

The compositions, including antibodies, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

In one aspect, disclosed herein are methods of treatment according to which a therapeutically effective quantity of an Ad according to the present description or of a host cell is administered to a patient requiring such a treatment. Such methods can comprise treating a host with one or more pharmaceutical entities prior to, or after infection with Ad.

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

Method of Treating Cancer

The disclosed Ad compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

The following examples are presented to illustrate the present invention and to assist one of the ordinary skill in making and using the same. The examples are not intended in any way to otherwise limit the scope of the invention.

Examples of the Viruses Illustrating the Matter of the Invention

Figure 2:
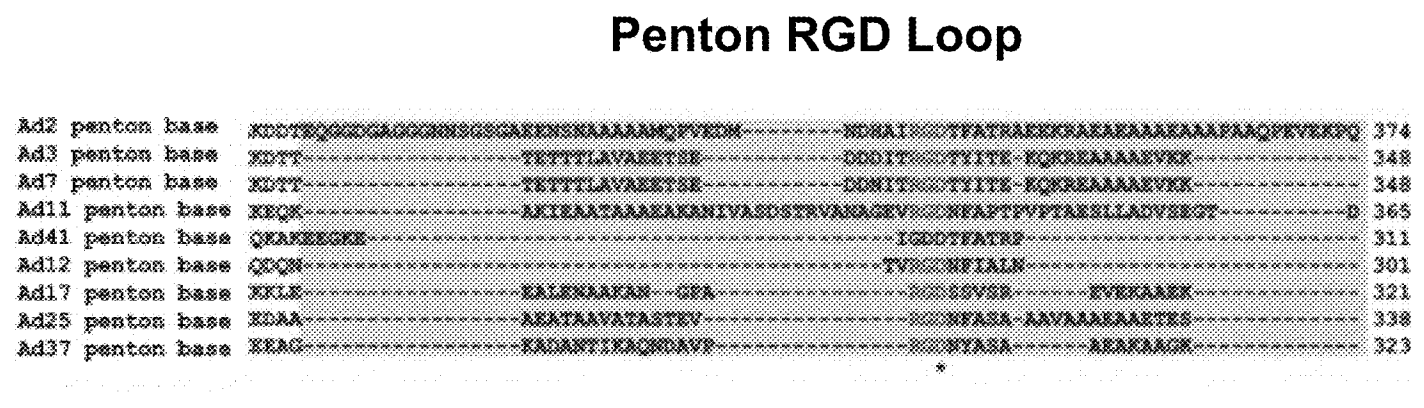

Adenovirus entry into the cell is a coordinated set of events, where a sequential interaction of virus capsid proteins and cellular receptors occurs. In this process, first, the virus fiber protein binds "primary" virus attachment receptor at the cell surface and for human species C Ad type 5 the receptor is CAR. For human species B Ad type 35 the receptor is CD46. Regardless of the primary virus attachment receptor interaction, all human Ad species, except for species F, bind cellular integrins via RGD amino acid motif in the virus penton base protein (FIG. 2). This interaction triggers virus internalization into the cell, which is absolutely required to initiate virus infection.

The canonical view of the function of virus-cellular integrin interaction is that this interaction is evolutionary conserved (the absolute majority of human and animal Ad species have RGD amino acid motif in RGD penton base loop, the selected serotypes are shown in FIG. 2) and from the vector development point of view, the presence of RGD amino acids in penton base protein is required for efficient cell infection.

The RGD motif, located within a flexible and highly variable loop of the penton base, is thought to be the functional moiety of the capsid that facilitates virus internalization into cells by promoting integrin clustering at the sites of virus attachment and viral endocytosis.

Ad5ΔRGD virus possesses a tri-amino acid deletion within flexible Ad5 penton RGD loop, which ablates Ad5 interaction with integrins via RGD motifs (Shayakhmetov et al., 2005).

Figure 6A:
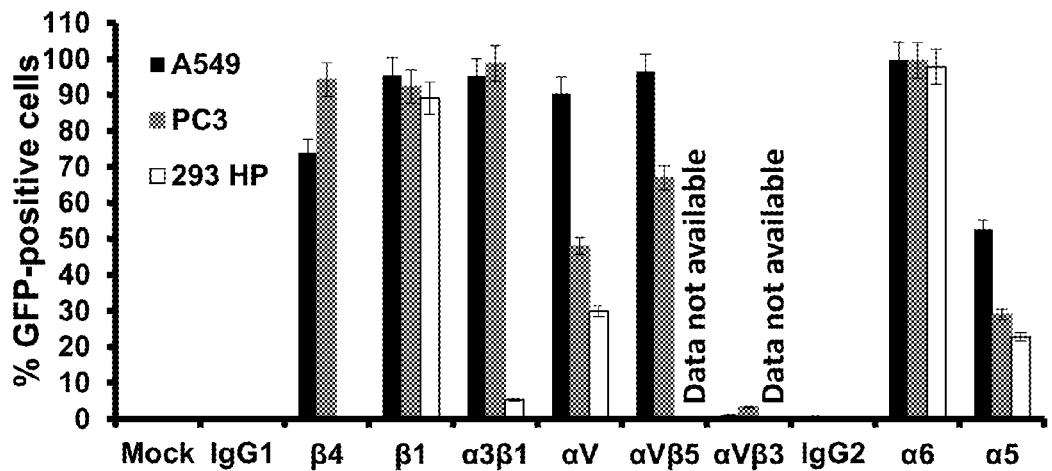
FIG. 6A shows the percentage of integrin-specific staining determined by flow cytometry analysis of 293, A549, and PC3 cell lines and detected by specific antibody staining.

Therefore, the examples of penton modifications that will abrogate Ad5 interactions with integrins include deletion of just three RGD amino acids from the penton RGD loop (FIG. 4A, dRGD sequence) (Shayakhmetov et al., 2005), the deletion of an entire integrin-interacting RGD motif-containing loop of Ad5 penton (FIG. 3A), or mutation of the penton in any way to prevent functional penton interactions with integrins. The one example of ablating the penton interaction with integrins via RGD motifs is a substitution of an RGD-motif-containing flexible loop of Ad5 with an amino acid sequence that contains no RGD motifs and that is able to selectively target Ad to a specific subset of integrins (FIG. 3B). These types of integrins include, but not limited to, α3β1, or αvβ5 integrins, which are highly expressed on tumor cells, but not on 293 cells (FIG. 6A).

An another example of ablation of Ad penton interaction with cellular β3-integrins is a substitution of amino acids in Ad penton RGD loop for amino acids from another protein or proteins, capable of binding to cellular integrins of non-β3-integrin class and possessing no RGD amino acid motifs.

As an example of the embodiment of the invention, we substituted 46 amino acids of the RGD motif-containing loop in the human adenovirus serotype 5 penton base for RGD-independent integrin-interacting sequences from human laminins 1 (50 amino acids, Ad-Lam1; SEQ. No. 1) and laminin-3 (54 amino acids, Ad-Lam3; SEQ. No. 2) (FIG. 4A). The analyses showed that these penton-mutated vectors could be rescued and amplified on HEK293 cells using standard virus production protocols.

Analysis of the protein composition of purified Ad particles for Ad-GFP vector, possessing naturally occurring in human Ad5 penton protein, or penton-mutated vectors Ad-ΔRGD (three RGD amino acids deleted in penton protein), Ad-Lam 1 (RGD loop amino acids deleted and substituted for an amino acid sequence from human laminin-1), and Ad-Lam3 (RGD loop amino acids deleted and substituted for amino acid sequence from human laminin-3, all as shown in FIG. 4A) demonstrated that all protein expected to be present in Ad particles are present in all vectors produced in 293 cells and purified to homogeneity using CsCl gradient methodology (FIG. 4B).

Figure 5A:
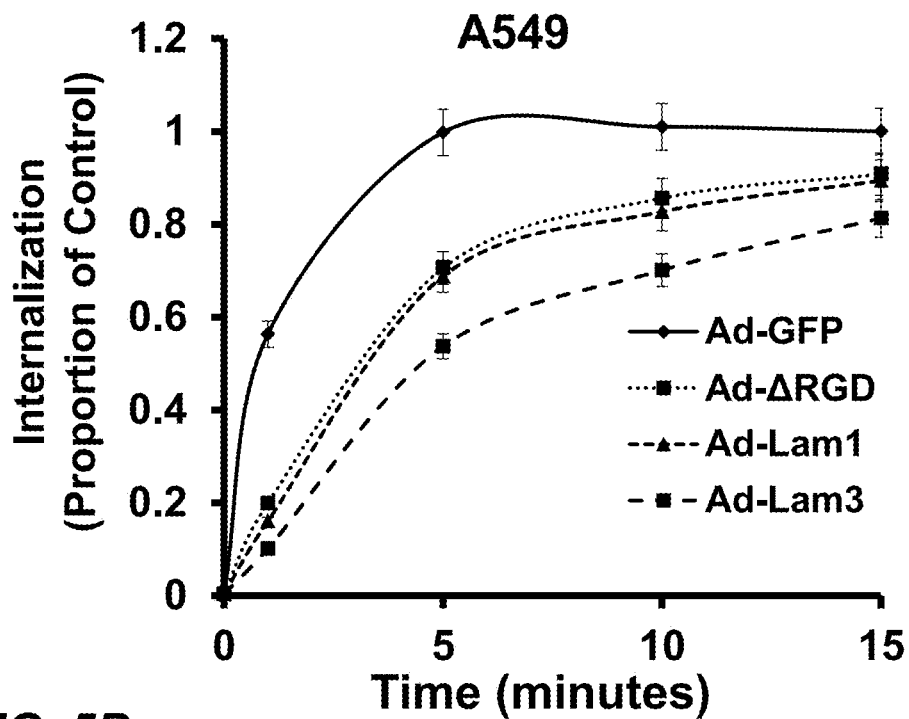
FIG. 5A is a graph describing internalization rate analysis for indicated vectors on A549 human lung carcinoma cell line. $2 \times 10^5$ cells incubated with indicated vectors 1000 vp/cell at 4° C. for 1 hour, washed, then allowed to internalize virus at 37° C. for indicated times before addition of neutralizing antibodies. Analyses were done as described in (Shayakhmetov et al., 2005).
Figure 5B:
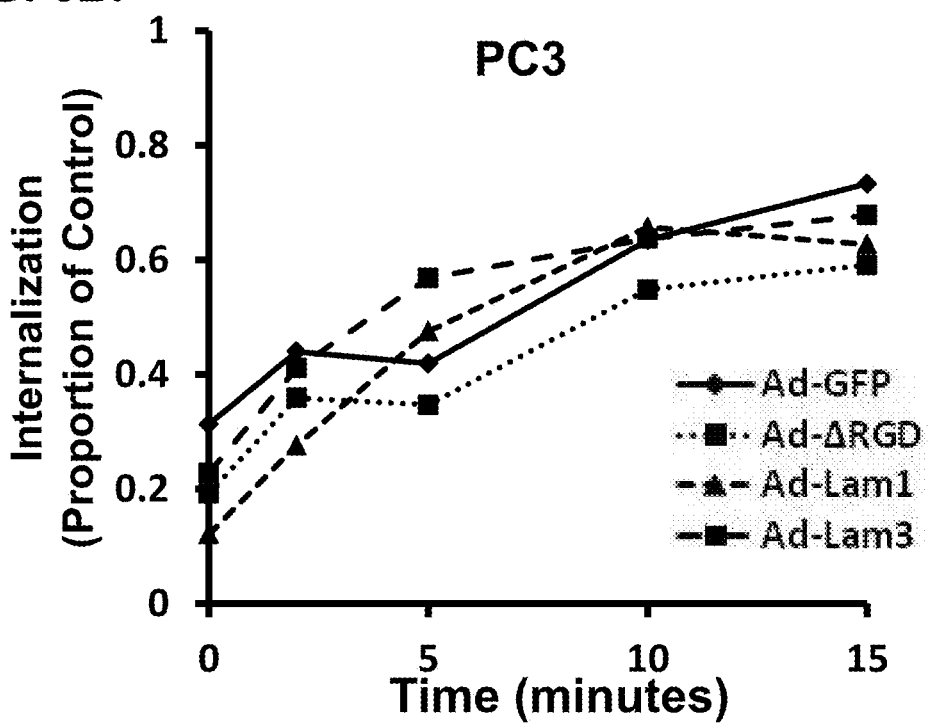
FIG. 5B is a graph describing internalization rate analysis for indicated vectors on PC3 prostate cancer cell line. $2 \times 10^5$ cells incubated with indicated vectors 1000 vp/cell at 4° C. for 1 hour, washed, then allowed to internalize virus at 37° C. for indicated times before addition of neutralizing antibodies. Analyses were done as described in (Shayakhmetov et al, 2005).

Furthermore, penton base-mutated vectors retained infectivity comparable to wild type vectors in prostate (PC3) carcinoma cells but reduced infectivity compared to Ad-GFP vector in human tumor lung (A549), providing evidence that mutation of RGD amino acids in Ad penton can have differential effects on virus infectivity in different types of cells (FIG. 5A, 5B).

Figure 6B:
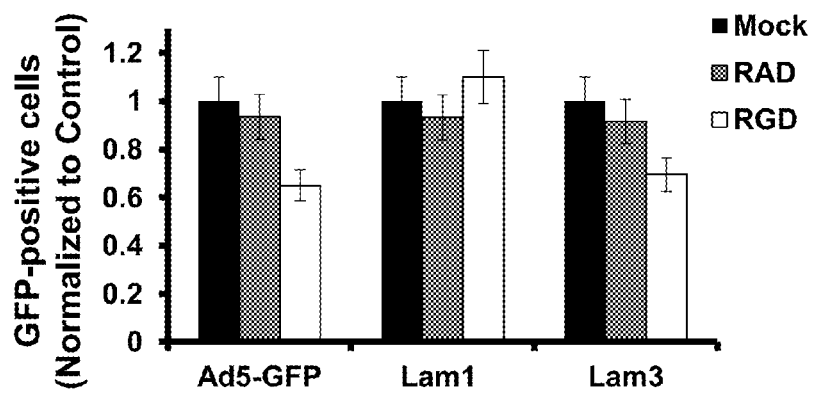
FIG. 6B is bars showing competition of virus infection of Ad-GFP and penton-mutated Ad-Lam1 and Ad-Lam3 vectors with soluble RGD, and SIKVAV peptides. $2 \times 10^5$ A549 cells exposed to 500 virus particles per cell at 4° C. after addition of synthetic peptides at 8 mM (RGD/RAD), washed, then allowed to internalize virus at 37° C. for 10 minutes before addition of neutralizing antibodies. Analyses of cell transduction were done by flow-cytometry 24 h after the virus infection.
Figure 6C:
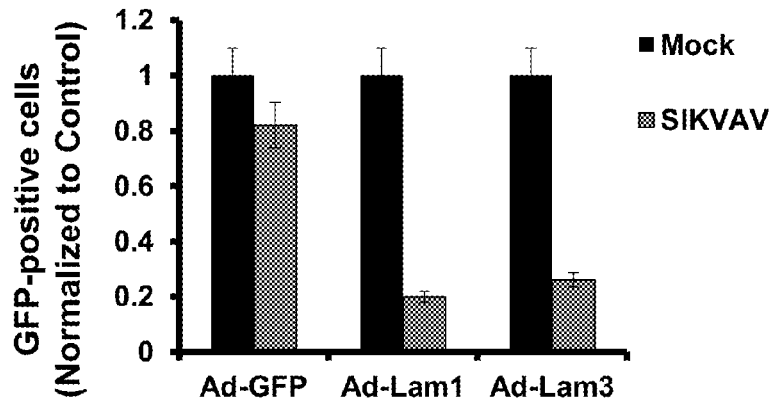
FIG. 6C is bars showing competition of virus infection of Ad-GFP and penton-mutated Ad-Lam1 and Ad-Lam3 vectors with soluble RGD, and SIKVAV peptides. $2 \times 10^5$ A549 cells exposed to 500 virus particles per cell at 4° C. after addition of synthetic peptide at 4 mM (SIKVAV), washed, then allowed to internalize virus at 37° C. for 10 minutes before addition of neutralizing antibodies. Analyses of cell transduction were done by flow-cytometry 24 h after the virus infection.

Competition studies with synthetic soluble RGD peptides that reduce wild-type virus interaction with cellular RGD-interacting integrins, or synthetic peptide SIKVAV that only blocks laminin-interacting intergins showed that Ad-Lam1 and Ad-Lam3 virus infection of cells cannot be blocked by RGD peptide, but it is efficiently blocked by SIKVAV peptide (FIG. 6B, 6C). In contrast, wild-type unmodified Ad variant, Ad-GFP, that possesses intact RGD amino acids in the penton protein infects cells efficiently in the presence of SIKVAV peptide, therefore demonstrating selectivity in integrin usage between the wild-type and new penton-mutated vectors.

Figure 7C:
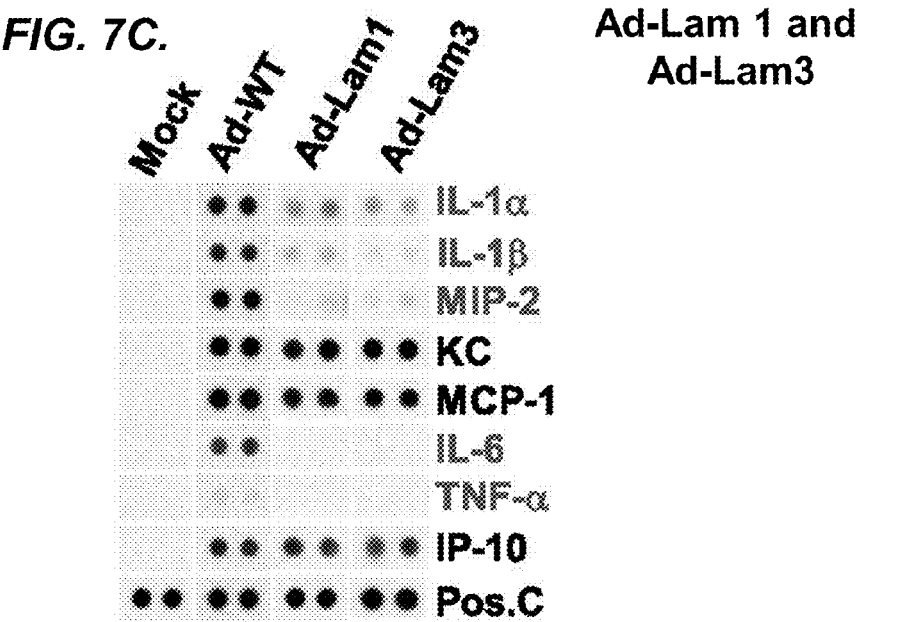
FIG. 7C shows activation of inflammatory cytokines and chemokines in the spleen of mice 1 hour after intravenous administration of indicated virus vectors at a dose of $2\times10^{10}$ virus particle per mouse, determined by proteome profiler antibody array. Note drastically reduced activation of IL-1α, IL-1β, IL-6, TNF-α, and MIP2 pro-inflammatory mediators after mouse injection with Ad-Lam1 and Ad-Lam3, compared to Ad-WT control vector with unmodified, naturally-occurring RGD-containing penton.

Intravenous injection of penton-mutated vectors into mice showed that unlike control vector with wild type penton, Ad-WT, penton-mutated vectors Ad-Lam1 and Ad-lam3 failed to activate key inflammatory cytokines, including IL-1α, IL-1β, IL-6, and TNF-α, and chemokines, including MIP-2, after intravenous administration in mice (FIG. 7C).

Figure 8:
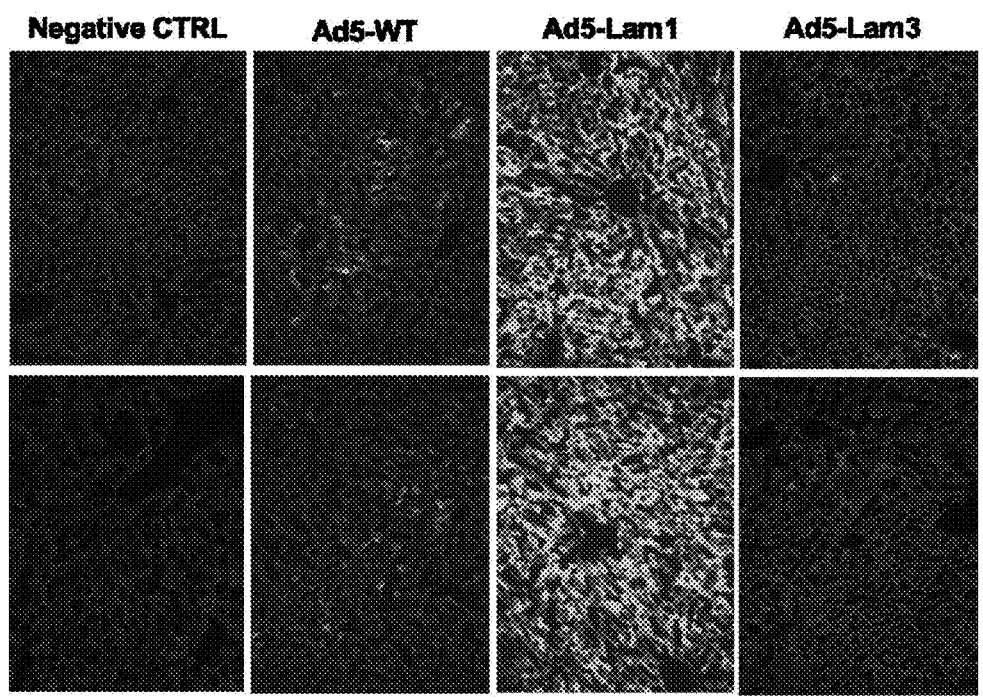
FIG. 8 shows analysis of virus-mediated GFP gene transfer into hepatocytes after intravenous injection of indicated vectors in mice analyzed on liver section 48 hours after virus injection at a dose of $5\times10^{10}$ virus particle per mouse. Note, highly efficient GFP gene transfer into hepatocytes after mouse injection with penton-mutated Ad5-Lam1 vector, but NOT other virus vectors, including wild-type virus with RGD amino acids in the penton (Ad5-WT).

Importantly, one of these vectors, Ad-Lam1 demonstrated high infectivity towards hepatocytes after intravenous virus administration (FIG. 8). This data provides direct evidence that the development of non-RGD-integrin-interacting vectors with improved gene transfer efficacy and reduced toxicity is not obvious, and highlighting utility of Ad5-Lam1 variant for in vivo gene delivery as exemplified here with liver cells, hepatocytes, with reduced systemic toxicity.

This example establishes both the conceptual and experimental feasibility for the development and reduction to practice of the adenovirus vectors with large domain substitutions in the penton base, which have a reduced capacity for activation of systemic inflammation but preserve the efficacy of gene transfer into target cells in vivo.

CITED REFERENCES

U.S. Patent Documents

U.S. Pat. No. 5,712,136 Wickham et al., 01/1998 435/456

Other Publications

1. Alemany, R., and Curiel, D. T. (2001). CAR-binding ablation does not change biodistribution and toxicity of adenoviral vectors. Gene Ther 8, 1347-1353.
2. Alemany, R., Suzuki, K., and Curiel, D. T. (2000). Blood clearance rates of adenovirus type 5 in mice. The Journal of general virology 81, 2605-2609.
3. Alonso-Padilla, J., Papp, T., Kajan, G. L., Benko, M., Havenga, M., Lemckert, A., Harrach, B., and Baker, A. H. (2015). Development of Novel Adenoviral Vectors to Overcome Challenges Observed With HAdV-5-based Constructs. Mol Ther.
4. Barouch, D. H., Kik, S. V., Weverling, G. J., Dilan, R., King, S. L., Maxfield, L. F., Clark, S., Ng'ang'a, D., Brandariz, K. L., Abbink, P., et al. (2011). International seroepidemiology of adenovirus serotypes 5, 26, 35, and 48 in pediatric and adult populations. Vaccine 29, 5203-5209.
5. Bergelson, J. M., Cunningham, J. A., Droguett, G., Kurt-Jones, E. A., Krithivas, A., Hong, J. S., Horwitz, M. S., Crowell, R. L., and Finberg, R. W. (1997). Isolation of a common receptor for Coxsackie B viruses and adenoviruses 2 and 5. Science 275, 1320-1323.
6. Bradley, R. R., Lynch, D. M., Iampietro, M. J., Borducchi, E. N., and Barouch, D. H. (2012). Adenovirus serotype 5 neutralizing antibodies target both hexon and fiber following vaccination and natural infection. J Virol 86, 625-629.
7. Di Paolo N C, B. L., Irons E E, Papayannopoulou T, Tomlinson S, Shayakhmetov D M (2014). IL-1a and complement cooperate in triggering local neutrophilic inflammation in response to adenovirus and eliminating virus-containing cells. PLoS Pathogens DOI: 10.1371/journal.ppat.1004035.
8. Di Paolo, N. C., Miao, E. A., Iwakura, Y., Murali-Krishna, K., Aderem, A., Flavell, R. A., Papayannopoulou, T., and Shayakhmetov, D. M. (2009). Virus binding to a plasma membrane receptor triggers interleukin-1 alpha-mediated proinflammatory macrophage response in vivo. Immunity 31, 110-121.
9. Gaggar, A., Shayakhmetov, D., and Lieber, A. (2003). CD46 is a cellular receptor for group B adenoviruses. Nature Medicine 9, 1408-1412.
10. Kojaoghlanian, T., Flomenberg, P., and Horwitz, M. S. (2003). The impact of adenovirus infection on the immunocompromised host. Rev Med Virol 13, 155-171.
11. Lieber, A., He, C. Y., Meuse, L., Schowalter, D., Kirillova, I., Winther, B., and Kay, M. A. (1997). The role of Kupffer cell activation and viral gene expression in early liver toxicity after infusion of recombinant adenovirus vectors. J Virol 71, 8798-8807.
12. Manickan, E., Smith, J. S., Tian, J., Eggerman, T. L., Lozier, J. N., Muller, J., and Byrnes, A. P. (2006). Rapid Kupffer cell death after intravenous injection of adenovirus vectors. Molecular Therapy 13, 108-117.
13. Nemerow, G. R. (2000). Cell receptors involved in adenovirus entry. Virology 274, 1-4.
14. Nemerow, G. R., and Stewart, P. L. (1999). Role of alpha(v) integrins in adenovirus cell entry and gene delivery. Microbiol Mol Biol Rev 63, 725-734.
15. Raper, S. E., Chirmule, N., Lee, F. S., Wivel, N. A., Bagg, A., Gao, G. P., Wilson, J. M., and Batshaw, M. L. (2003). Fatal systemic inflammatory response syndrome in a ornithine transcarbamylase deficient patient following adenoviral gene transfer. Mol Genet Metab 80, 148-158.
16. Raper, S. E., Yudkoff, M., Chirmule, N., Gao, G. P., Nunes, F., Haskal, Z. J., Furth, E. E., Propert, K. J., Robinson, M. B., Magosin, S., et al. (2002). A pilot study of in vivo liver-directed gene transfer with an adenoviral vector in partial ornithine transcarbamylase deficiency. Hum Gene Ther 13, 163-175.
17. Roberts, D. M., Nanda, A., Havenga, M. J. E., Abbink, P., Lynch, D. M., Ewald, B. A., Liu, J., Thorner, A. R., Swanson, P. E., Gorgone, D. A., et al. (2006). Hexon-chimaeric adenovirus serotype 5 vectors circumvent pre-existing anti-vector immunity. Nature 441, 239-243.
18. Roelvink, P. W., Lizonova, A., Lee, J. G., Li, Y., Bergelson, J. M., Finberg, R. W., Brough, D. E., Kovesdi, I., and Wickham, T. J. (1998). The coxsackievirus-adenovirus receptor protein can function as a cellular attachment protein for adenovirus serotypes from subgroups A, C, D, E, and F. J Virol 72, 7909-7915.
19. Shayakhmetov, D. M., Eberly, A. L., Li, Z. Y., and Lieber, A. (2005). Deletion of penton RGD motifs affects the efficiency of both the internalization and the endosorne escape of viral particles containing adenovirus serotype 5 or 35 fiber knobs (vol 79, pg 1053, 2005). Journal of Virology 79, 4553-4553.
20. Shayakhmetov, D. M., Li, Z. Y., Ni, S., and Lieber, A. (2004). Analysis of adenovirus sequestration in the liver, transduction of hepatic cells, and innate toxicity after injection of fiber-modified vectors. J Virol 78, 5368-5381.
21. Shenk, T. (1996). Adenoviridea. In Fields Virology, B. N. Fields, Knipe, D. M., Howley, P. M., ed. (Philadelphia: Lippincott-Raven Publisher), pp. 2111-2148.

22. Shenk, T. (2001). Adenoviridae. in Field's Virology (D. M. Nipe and P. M. Howley, Eds.), 2265-2328.
23. Wickham, T. J., Mathias, P., Cheresh, D. A., and Nemerow, G. R. (1993). Integrins alpha v beta 3 and alpha v beta 5 promote adenovirus internalization but not virus attachment. Cell 73, 309-319.
24. Worgall, S., Wolff, G., Falck-Pedersen, E., and Crystal, R. G. (1997). Innate immune mechanisms dominate elimination of adenoviral vectors following in vivo administration. Hum Gene Ther 8, 37-44.

What is claimed is:

1. A recombinant, double-stranded, adenovirus, comprising a single virus genomic DNA molecule comprising a specific mutation in a coding sequence of a penton base protein to ablate adenovirus (Ad) interactions with cellular β3-integrins, wherein the mutation reduces activation of inflammation after intravascular virus delivery and wherein the recombinant, double-stranded, adenovirus retains infectivity comparable to wild-type adenovirus, and wherein the single virus genomic DNA molecule comprises a nucleotide sequence encoding SEQ ID NO:1 or SEQ ID NO:2.

2. The recombinant double-stranded adenovirus of claim 1, wherein the adenovirus is formulated for intravenous administration.

3. The recombinant, double-stranded adenovirus of claim 1, wherein the single virus genomic DNA molecule comprises the nucleotide sequence encoding SEQ ID NO:1.

4. The recombinant, double-stranded adenovirus of claim 1, wherein the single virus genomic DNA molecule comprises the nucleotide sequence encoding SEQ ID NO:2.

5. A recombinant adenovirus comprising a mutated penton base protein comprising the amino acid sequence of SEQ ID NO:1, wherein the recombinant adenovirus has reduced activation of inflammation after intravascular administration compared to wild-type adenovirus.

6. The recombinant adenovirus of claim 5, wherein the recombinant adenovirus retains infectivity comparable to wild-type adenovirus.

7. The recombinant adenovirus of claim 5, wherein the adenovirus further comprises a mutated fiber protein.

8. A recombinant adenovirus comprising a mutated penton base protein comprising the amino acid sequence of SEQ ID NO:2, wherein the recombinant adenovirus has reduced activation of inflammation after intravascular administration compared to wild-type adenovirus.

9. The recombinant adenovirus of claim 8, wherein the recombinant adenovirus retains infectivity comparable to wild-type adenovirus.

10. The recombinant adenovirus of claim 8, wherein the adenovirus further comprises a mutated fiber protein.

* * * * *

SEQUENCE LISTING

```
<160> NUMBER OF SEQ ID NOS: 4

<210> SEQ ID NO 1
<211> LENGTH: 61
<212> TYPE: PRT
<213> ORGANISM: Artificial
<220> FEATURE:
<223> OTHER INFORMATION: Human adenovirus serotype 5 penton-human
      laminin 1 chimera

<400> SEQUENCE: 1

Asn Ala Ala Ala Ser Gly Thr Lys Leu Leu Ile Ser Gln Ala Arg Lys
1               5                   10                  15

Gln Ala Ala Ser Ile Lys Val Ala Val Ser Ala Asp Arg Asp Cys Ile
            20                  25                  30

Arg Ala Tyr Gln Pro Gln Ile Ser Ser Thr Asn Tyr Asn Thr Leu Thr
        35                  40                  45

Gly Ser Thr Gly Gly Ala Lys Pro Gln Lys Lys Pro Val
    50                  55                  60

<210> SEQ ID NO 2
<211> LENGTH: 68
<212> TYPE: PRT
<213> ORGANISM: Artificial
<220> FEATURE:
<223> OTHER INFORMATION: Human adenovirus serotype 5 penton-human
      laminin 3 chimera

<400> SEQUENCE: 2

Asn Ala Ala Ala Ser Gly Thr Arg Glu Leu Ile Gln Ala Arg Asp Ala
1               5                   10                  15

Ala Ser Lys Val Ala Val Pro Met Arg Phe Asn Gly Lys Ser Gly Val
            20                  25                  30

Glu Val Arg Leu Pro Asn Asp Leu Glu Asp Leu Lys Gly Tyr Thr Ser
        35                  40                  45

Leu Ser Leu Gly Ser Thr Gly Gly Ala Pro Glu Val Glu Lys Pro Gln
    50                  55                  60

Lys Lys Pro Val
65

<210> SEQ ID NO 3
<211> LENGTH: 15
<212> TYPE: PRT
<213> ORGANISM: Artificial
<220> FEATURE:
<223> OTHER INFORMATION: Human adenovirus serotype 5 penton chimera - 1

<400> SEQUENCE: 3

Met Gly Ser Gly Cys Asn Gly Gln Gly Glu Gln Cys Ala Ala Ala
1               5                   10                  15

<210> SEQ ID NO 4
<211> LENGTH: 15
<212> TYPE: PRT
<213> ORGANISM: Artificial
<220> FEATURE:
<223> OTHER INFORMATION: Human adenovirus serotype 5 penton chimera - 2
```

```
<400> SEQUENCE: 4

Met Gly Ser Gly Arg Lys Lys Arg Arg Gln Arg Arg Ala Ala Ala
1               5                   10                  15
```